United States Patent

Abramo et al.

[11] Patent Number: 5,574,031
[45] Date of Patent: Nov. 12, 1996

[54] PIPERAZINE CARBOXAMIDES

[75] Inventors: Lisbeth Abramo, Bjärred; Torbjörn Lundstedt, Löddeköpinge; Curt Nordvi, Malmö; Knut G. Olsson, Malmö; Martin Brodszki, Malmö, all of Sweden

[73] Assignee: Pharmacia Aktiebolag, Stockholm, Sweden

[21] Appl. No.: 374,797
[22] PCT Filed: Jul. 22, 1993
[86] PCT No.: PCT/SE93/00639
§ 371 Date: Jan. 31, 1995
§ 102(e) Date: Jan. 31, 1995
[87] PCT Pub. No.: WO94/03436
PCT Pub. Date: Feb. 17, 1994

[30] Foreign Application Priority Data

Jul. 31, 1992 [SE] Sweden .................. 9202266

[51] Int. Cl.⁶ .................. A61K 31/495; A61K 31/55; C07D 295/195; C07D 243/08
[52] U.S. Cl. .................. 514/212; 514/218; 514/235.8; 514/252; 514/255; 540/575; 540/598; 544/121; 544/359; 544/360; 544/364; 544/372; 544/390
[58] Field of Search .................. 544/121, 359, 544/360, 364, 372, 398; 540/575, 598; 514/212, 218, 235.8, 252, 255

[56] References Cited

U.S. PATENT DOCUMENTS

| 4,082,755 | 4/1978 | van Wijngaarden | 260/293.6 |
|---|---|---|---|
| 4,308,387 | 12/1981 | Björk et al. | 544/390 |
| 4,374,990 | 2/1983 | Weber et al. | 544/376 |
| 4,766,125 | 8/1988 | Van Daele | 514/255 |
| 4,874,765 | 10/1989 | Lapis et al. | 514/255 |
| 5,026,853 | 6/1991 | Van Daele et al. | 544/398 |

FOREIGN PATENT DOCUMENTS

| 1237128 | 5/1988 | Canada . |
|---|---|---|
| WO91/07967 | 6/1991 | WIPO . |

OTHER PUBLICATIONS

Cecil Textbook of Medicine, 19th ed. (1992), Wyngaarden, M. D. editor, pp. 2075–2078.

*Primary Examiner*—Philip I. Datlow
*Attorney, Agent, or Firm*—Birch, Stewart, Kolasch & Birch, LLP

[57] ABSTRACT

Compounds of general formula (I) are useful for treating mental disorders, wherein $R_1$ and $R_2$ are the same or different and selected from hydrogen or lower alkyl; Ar are the same or different and selected from pyridyl and phenyl groups, n is 1 or 2, X is nitrogen or methine. When X is nitrogen, Y is methylene. When X is methine, Y is selected from nitrogen or oxygen. A is selected from carboxylic derivatives. The pharmacologically active salts of formula (I) are also embraced.

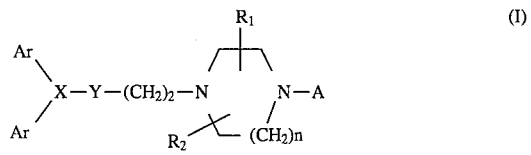

9 Claims, No Drawings

PIPERAZINE CARBOXAMIDES

This application is the 35 USC 371 National Style of international application PCT/SE93100639 filed on Jul. 22, 1993 and published as WO94/03436 on Feb. 17, 1994.

BACKGROUND

There is an urgent need for efficient drugs in the treatment of mental disorders which are more effective and which have fewer side effects than the drugs in clinical use today. Antipsychotic drugs in current use produce a range of troublesome extrapyramidal movement disorders (e.g. acute dystonic reactions and tardive dyskinesia) and are poor in ameliorating the negative symptoms (e.g. restricted or blunted emotional arousal) of schizophrenia. The main disadvantage of the antidepressants is that they fail to alleviate depression in 30 to 40% of patients. Anxiolytics are commonly associated with addictive properties.

PRIOR ART

Various piperazine derivates pharmacologically active in the central nervous system are known in the art. Some representative examples can be mentioned. The U.S. Pat. No. 4,308,387 discloses amperozide which has shown useful antipsychotic properties in clinical investigations. Amperozide has a limbic profile of action.

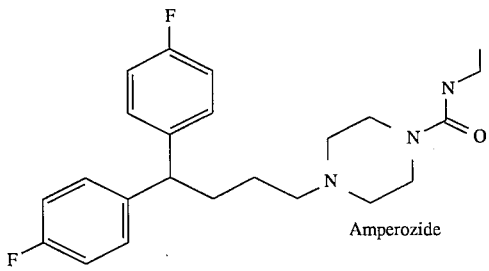

Amperozide

DESCRIPTION OF THE INVENTION

According to the invention there are provided novel compounds having the general formula (I).

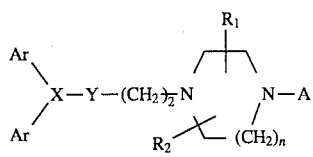

wherein Ar are the same or different and selected from

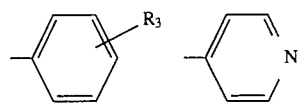

wherein $R_3$ is halogen or hydrogen.
$R_1$ and $R_2$ are the same or different and selected from hydrogen or alkyl;
n is 1 or 2,
X is nitrogen or methine
When X is nitrogen Y is methylene.
When X is methine Y is selected from nitrogen or oxygen;
A is selected from the following carboxylic derivatives:

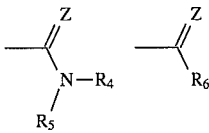

wherein $R_4$ and $R_5$ are the same or different and selected from hydrogen, alkyl, cycloalkyl or aryl. Z is selected from sulfur or oxygen. $R_6$ is selected from

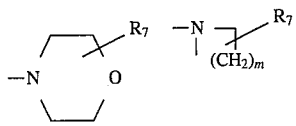

wherein m is 1, 2, 3 or 4.
$R_7$ is selected from hydrogen or lower alkyl. And the pharmacologically active salts thereof. Used in the foregoing definitions the term lower alkyl is meant to include straight and branched, saturated and unsaturated hydrocarbon groups having from 1 to 5 carbon atoms; the term cycloalkyl is meant to include cyclic, saturated and unsaturated hydrocarbon groups have from 3 to 8 carbon atoms. the term lower alkoxy is meant to include straight or branched, saturated or unsaturated alkoxy groups having from 1 to 5 carbon atoms: the term halogen is meant to include fluoro, and bromo.

The compounds of formula (I) have basic properties and, consequently, they may be converted to their therapeutically active acid addition salts by treatment with appropriate acids; e.g. inorganic acids such as hydrochloric, hydrobromic, sulfuric, nitric and phosphoric acid, or organic acids such as acetic, propanoic, glycolic, lactic, malonic, oxalic, succinic, fumaric, tartaric, citric and pamoic acid.

Conversely, the salt form can be convened into the flee base form by treatment with alkali.

The compounds of formula (I) and their pharmaceutically acceptable salts have valuable pharmacological properties. making them useful for the treatment of mental disorders such as psychoses, depression, anxiety and drug abuse. Stress and anxiety in animals can also be treated.

The compounds of the present invention show psychotropic properties. They have found to be selective 5-HT$_2$ antagonists.

METHODS OF PREPARATION

The compounds having the general formula (I) may be prepared by conventional methods.
Method 1

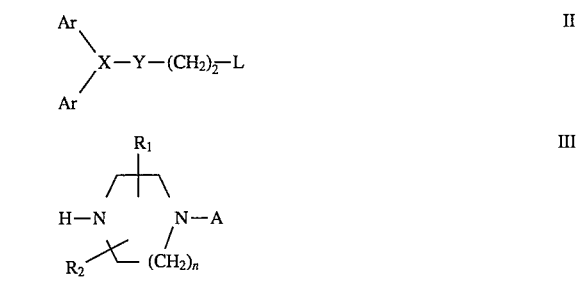

A compound of formula (II), wherein Ar, X and Y are as previously defined and L is a suitable leaving group such as halogen and alkyl- or arylsulfonate is reacted with a compound of formula (III) wherein $R_1$, R2, A and n are as defined previously. The reactions may be carried out using standard N-alkylating procedures.

Method 2

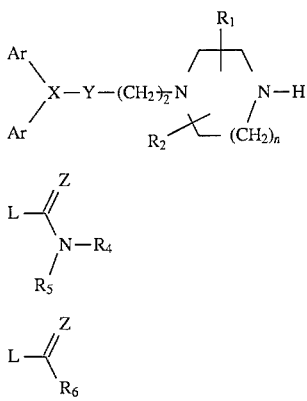

A compound of formula IV, wherein Ar, $R_1$, $R_2$, X, Y, Z and n are as previously defined is reacted with a compound of formula V, VI, wherein $R_4$, $R_5$, $R_6$ and Z are as previously defined and L is a suitable leaving group.

Method 3

A compound of formula IV is reacted with a compound of formula VII wherein $R_4$ is as previously defined.

Method 4

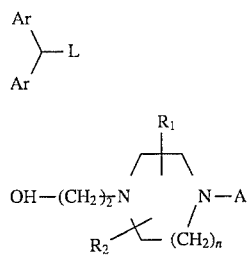

A compound of formula VIII, wherein Ar is as previously defined is reacted with a compound of formula IX, wherein n and A are as previously defined, L is hydroxy or a leaving group.

Method 5

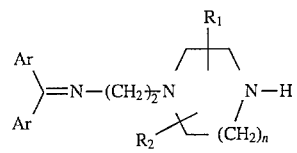

A compound of formula X wherein Ar, n, $R_3$ and $R_4$ are as previously defined is reacted with a compound of formula V or VI to yield a product of formula XI.

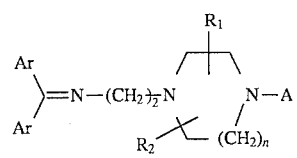

wherein Ar, n, $R_1$, $K_2$ and A are as previously defined. The compound XI is reduced to yield a compound of formula XII.

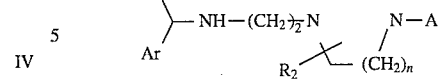

Wherein Ar, $R_3$, $R_4$, n and A are as previously defined.

Method 6

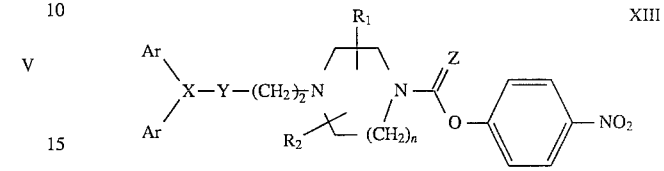

A compound of formula XIII wherein Ar, X, Y, $R_1$, R2 and Z are as previously defined is reacted with a secondary amine to yield a product described by formula (I).

Method 7

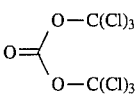

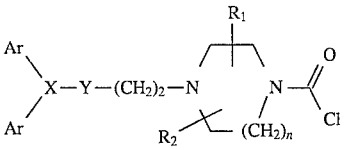

A compound of formula IV is reacted with triphosgene (XIV) to yield a product of formula (XV), wherein Ar, n, X, Y, $R_1$ and $R_2$ are as previously defined, which is reacted with a secondary amine to yield a product described by formula (I).

EXAMPLES

The following examples are intended to illustrate but not limit the scope of the invention, although the compounds named are particular interest for our intended purposes. These compounds have been designated by a number code. a:b, where a means the number of the example, wherein the preparation of the compound in question is described. and b refers to the order of the compounds prepared according to that example. Thus, compound 1:2 means the second compound prepared according to example 1.

The structures of the compound are confirmed by NMR masspectra and elementary analysis. When melting points are given, these are uncorrected.

Example 1:1

1-{3-[Bis(p-fluorophenyl)amino]propyl}-N-ethyl-4-piperazine-carboxamide hydrochloride.

4.7 g (0.3 mol) of N-ethylpiperzinecarboxamide. 13.4(0.036 mol) of 3-[Bis-(p-fluorophenyl)amino]propyiiodide and 5 g (0.060 mol) of $NaHCO_3$ were refluxed for 48 h in ethanol.

After cooling, the reaction mixture was filtrated. Evaporation of the solvent yielded the crude base. 3.2 g of the free base was dissolved in 40 ml of diethyl ether. The hydrochloride was precipitated with excess of hydrochloric acid in ethanol. Recrystallisation in 2-butanone yielded 2.7 g of the title compound (1:1) m.p. 164°–165° C.

Example 2:1

4-{2-[(4,4'Difluorobenzhydryl)oxy}-ethyl]-N-n-octyl-1-piperazine-carboxamide hydrochloride 5.6 g (0.017 mol) 2-[(4,4'Difluorobenzhydryl)oxy]ethyl piperazine. 4.5 g (0.018 mol) phenyl-octylcarbamate and 2.8 g of potassium carbonate was stirred and refluxed together with 60 ml of toluene for about 1 h. The reaction mixture was filtered. The filtrate was washed three times with water and then with brine. The organic layer was dried over sodium sulphate and filtered. The solvent was removed from the filtrate by evaporation to yield an oil. 6.5 g of the oil was dissolved in 70 ml of ethyl acetate. The hydrochloride was precipitated with excess of hydrochloric acid in ethanol. Recrystallisation from isopropanolether yielded 5.3 g of the titled compound (2:1), m.p. 171°–172° C.

In essentially, the same method was used to prepare the following compound.

2:2
1-[2-[(4,4'-Difluorobenzhydryl)amino]ethyl]-4-(N-isopropylcarbamoyl)piperazine 2.25 hydrochloride m.p. 192°–193° C.

Example 3:1

4-[2-[(4,4'Difluorobenzhydryl)oxy]-ethyl]-N-ethyl-1-piperazinecarboxamide hydrochloride. 5 g 2-[(4,4'Difluorobenzhydryl)oxy]-ethyl-piperazine and 100 ml of ether were placed in a three-necked flask. 1.1 g ethylisocyanate dissolved in 20 ml of ether was added drop by drop to the flask. The reaction mixture was stirred for 2 h at room temperature.

The solvent was evaporated. The residue was dissolved in ether. The hydrochloride was precipitated with excess of hydrochloride in ethanol. Recrystallisation from iso-propanol yielded 4.5 g of the title compound (3:1), m.p. 191°–192° C.

In essentially, the same method was used to prepare the following compounds.

3:2
4-[2-[(4,4'Difluorobenzhydryl)oxy]-ethyl]-N-cyclohexyl-1-piperazinecarboxamide hydrochloride m.p. 199°–200° C.

3:3
4-[2-[(4,4'Difluorobenzhydryl)oxy]-ethyl]-N-phenyl-1-piperazinecarboxamide hydrochloride m.p. 211°–212° C.

3:4
4-[2-[(4,4'Difluorobenzhydryl)oxy]-ethyl]-N-methyl-1-piperazinethiocarboxamide hydrochloride m.p. 193°–194° C.

3:5
1-[3-(N-4-pyridyl-4-fluoroanilino)propyl]-N-ethyl-4-piperazinecarboxamide dioxalate m.p. 172°–173° C.

3:6
1-[3-(N-pyridyl-14-fluoroanilino)propyl]-N-phenyl-4-piperazinecarboxamide difumarate m.p. 151°–155° C.

3:7
1-[3-(N,N-Di(p-fluorophenyl)amino)propyl]-N-cyclohexyl-14-piperazinecarboxamide hydrochloride, hydrate 167°–170° C.

3:8
1-[3-(N,N-Di(p-fluorophenyl)amino)propyl]-N-phenyl-4-piperazinecarboxamide hydrochloride, hemihydrate 187°–190° C.

3:9
1-[3-(N,N-Di(p-fluorophenyl)amino)propyl]-N-phenyl-4-piperazinethiocarboxamide 1.5 hydrochloride m.p. 187°–188° C.

3:10
1-[3-(N-pyridyl-4-fluoroanilino)propyl]-N-cyclohexyl-4-piperazinecarboxamide difumarate m.p. 175° C. (dec.)

Example 3b:1

4-{2-[(4,4-Difluorobenzhydryl)oxy]ethyl}-1-piperazinecarboxamide hydrochloride.

A solution of 4-{2-[(4,4-Difluorobenzhydryl)oxy]ethyl}piperazine, (4.0 g 0.012 mol) in 20 ml glacial acetic acid was cooled to 0° C. at which time 3 g (0.036 mol) of potassium cyanate dissolved in 20 ml water was added. The resulting solution was stirred at room temperature for 24 hours. and then diluted with 100 ml of water. 20% aqueous sodium bicarbonate solution was added to reach pH 7 and then extracted three times with 200 ml of ethyl acetate. The combined organic layers were washed with brine, dried over anhydrous sodium sulphate and the solvent was evaporated. The residue 4 g (0.011 mol) was purified by silica gel column chromatography (dichloromethane: methanol 10:0.9) and the pole fractions of interest were combined and concentrated, 3 g of an oil was obtained.

After adding of 20 ml of ethanol and cooling, the substance solidified. The solid formed was collected by filtration and washed with two 20 ml portions of cold ethanol. The solid was dissolved in ether and 5-N HCl in ethanol was added. A white solid was obtained by recrystallisation from ethanol:ether. 3 g of the title compound (3b:1) were obtained m.p 116°–119° C.

Example 4:1

4-{2-[(4.4'-Difluorobenzhydryl)oxy]ethyl}-N-methyl-1-piperazinecarboxamide hydrochloride 3.7 g (0.020 mol) of 1-(2-hydroxoethyl)-N-methyl-1-piperazinecarboxamide and 2.4 g (0.010 mol) of 4-fluorobenzhydrylchloride were stirred at 165°–170 C. (temperature of oil bath) for 45 min. under nitrogen. After cooling, 60 ml of water and 60 ml of toluene were added to the reaction mixture. The phases were separate. Evaporation of the organic solvent yielded the crude base which was purified by flash chromatography and isolated as an oil 2.0 g of the free base was dissolved in 20 ml of ether. The dihydrochloride was precipitated with excess of hydrochloric acid in ethanol. Recrystallisation in isopropanol:diethylether 3:1 yielded 1.5 g of the titled compound (4:1), m.p.202°–203 C.

Example 5:1

1-{2-[(4,4'Difluorobenzhydryl)amino]ethyl}-N-cyclohexyl-4-piperazinecarboxamide 2.25 hydrochloride 3.2 g (0.01 ml) of 1-[2[(4,4'-Difluorobenzhydryl)amino]ethyl]piperazine and 80 ml of ether were placed in a three-necked flask. 1.4 g (0.01 ml) cyclohexylisocyanate dissolved in 20 ml of ether was added drop by drop to the flask. The reaction mixture was stirred for 2 h at room temperature and crystals were formed. The product was then filtered off.

2.2 g (0.05 ml) of the crystals was dissolved in 20 ml of methanol and 1.0 g (0.03 ml) of $NaBH_4$ were added and refluxed for 1 h. After cooling, the solvent was evaporated and the residue was dissolved in water and ether. The ether layer was washed three times with water and dried.

The hydrochloride was precipitated with hydrochloric acid in ethanol. Recrystallisation from isopropanol yielded 1.8 g of the titled compound (5:1) m.p. 96°–97° C.

In essentially, the same method was used to prepare the following compounds.

5:2
1-[2-[(4,4'-Difluorobenzhydryl)amino]ethyl]-4-(N-butyl-carbamoyl)piperazine 2.25 hydrochloride m.p. 165°–167° C.

5:3
1-[2-[(4,4-Difluorobenzhydryl)amino]ethyl]-N-phenyl-4-piperazinethiocarboxamide m.p. 133°–134° C.

Example 6:1

1-{2-[(4,4'-Difluorobenzhydryl)oxy]ethyl}-(4-morpholino-carbonyl)piperazine hydrochloride 10 g of 4-[2-[(4,4'-Difluorobenzhydryl)oxy]ethyl]-p-nitrophenylpiperazinecarbamate was heated at 140° C. together with 20 ml of morpholine for 12 h. The excess of morpholine was evaporated. The residue was dissolved in ether and washed with brine, 10% NaOH, brine. The solvents were evaporated and the crude base was obtained as an oil.

The oil was dissolved in ether and the hydrochloride was precipitated by hydrochloric acid in ethanol. Recrystallisation from methanol/acetone 1:10 yielded 8.0 g of the titled compound (6:1), m.p. 208°–209° C.

In essentially, the same method was used to prepare the following compounds

6:2
1-[2-[(4,4'-Difluorobenzhydryl)oxy]ethyl]-4-(pyrrolidino-carbonyl)piperazine hydrochloride m.p. 170°–171 ° C.

6:3
1-[2-[(4,4'-Difluorobenzhydryl)amino]ethyl]-4-(4-methylpiperidinocarbonyl)piperazine 2.5 hydrochloride m.p. 219°–221° C.

6:4
1-[2-[(4,4'-Difluorobenzhydryl)amino]ethyl]-4-(N,N-dipentylcarbamoyl)piperazine 2.5 hydrochloride m.p. 113°–115° C.

6:5
1-[3-(N,N-Di(p-fluorophenyl)amino)propyl]-N,N-diethyl-4-piperazinecarboxamide hydrochloride m.p. 141°–142° C.

Example 7:1

1-{2-[(4,4'-Difluorobenzhydryl)oxy}ethyl}-4-(N,N-diethylcarbamoyl)piperazine hydrochloride.

A solution of 5 g (0.015 mol) of 1-[2-[(4,4'-Difluorobenzhydryl)oxy]ethyl]piperazine. 50 ml toluene and 3 ml (0.02 mol) triethylamine was added dropwise to a solution of 1.5 g (0.005 mol) triphosgene in 100 ml toluene at 5°–10° C. for 1 h. The mixture was allowed to stand at room temperature for 16 h and then washed with 1-N NaOH and water, dried over sodium sulphate. Evaporation of the solvent yielded the crude base as an oil.

The oil was dissolved in ether and the hydrochloride was precipitated with excess of hydrochloric acid in ethanol. Recrystallisation from ethyl acetate: 2-butanone (3:1) yielded 2.5 g of the title compound (7:1) m.p. 158°–160° C. (dec.).

In essentially, the same method was used to prepare the following compound.

7:2
1-[2-[(4,4'-Difluorobenzhydryl)oxy]ethyl]-4-(N,N-dipropylcarbamoyl)piperazine hydrochloride m.p. 125°–127° C.

Example 8

Test 1. Affinity to 5-HT$_2$ receptors

The binding assay is carried out essentially as described by Leysen et al. (Mol. Pharmacol. 21,301-14, 1982) using $^3$H-ketanserin as ligand.

Test 2 Affinity to D$_2$-receptors.

The binding assay is carried out essentially as described by Leysen et al. (Mol. Pharmacol. 21,301-14, 1982) using $^3$H-spiroperidol as ligand.

TABLE 1

| Compound | 5-HT$_2$ K$_i$ (nM) | D$_2$ K$_i$ (nM) |
| --- | --- | --- |
| 3:1 | 60 | >10000 |
| 3:4 | 20 | 1600 |
| 6:2 | 15 | 1780 |
| Amperozide | 17 | 540 |

The compounds listed in Table 1 are not given for purpose of limiting the invention thereto but only to exemplify the useful pharmacological activities of compounds within the scope of formula (I).

Example 9

The following formulations are representative for all of the pharmacologically active compounds of this invention. Example of a suitable capsule formulation:

|  | Per capsule, mg |
| --- | --- |
| Active ingredient, as salt | 10 |
| Lactose | 250 |
| Starch | 120 |
| Magnesium stearate | 5 |
| Total | 385 |

In case of higher amounts of active ingredients, the amount of lactose used may be reduced.

Example of a suitable tablet formulation

|  | Per tablet, mg |
| --- | --- |
| Active ingredient, as salt | 10 |
| Potato starch | 90 |
| Collodial Silica | 10 |
| Talc | 20 |
| Magnesium stearate | 2 |
| 5% aqueous solution of gelatine | 25 |
| Total | 157 |

Solutions for parenteral applications by injection can be prepared in a aqueous solution of a water-soluble pharmaceutically acceptable salt of the active substance preferably in a concentration of from about 0.5% to about 5% by weight. These solutions may also contain stabilising agents and/or buffering agents and may conveniently be provided in various dosage unit ampoules.

We claim:
1. A compound having the formula (I)

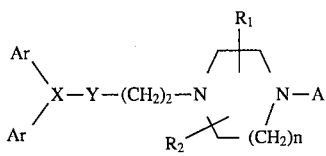

wherein Ar are the same or different and selected from

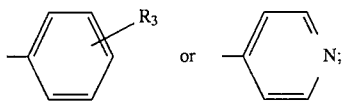

$R_3$ is halogen or hydrogen;
$R_1$ and $R_2$ are the same or different and selected from hydrogen or lower alkyl;
n is 1 or 2;
X is nitrogen or methine;
when X is nitrogen Y is methylene and when X is methine Y is selected from NH or oxygen;
A is selected from the following carboxylic derivatives:

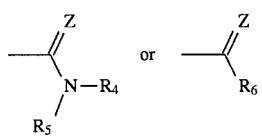

wherein $R_4$ and $R_5$ are the same or different and selected from hydrogen, alkyl, cycloalkyl or aryl, Z is selected from sulfur or oxygen, $R_6$ is selected from

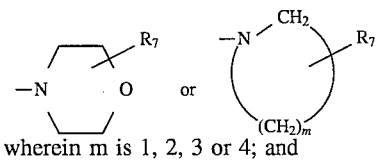

wherein m is 1, 2, 3 or 4; and
$R_7$ is selected from hydrogen or lower alkyl; and pharmacologically active salts thereof.

2. The compound according to claim 1 wherein n is 1.
3. The compound according to claim 1 or 2, wherein $R_1$ and $R_2$ are hydrogen.
4. The compound according to claim 3, wherein X is methine.
5. The compound according to 4, wherein Y is oxygen.
6. The compound according to claim 5, wherein $R_4$ and $R_5$ are selected from hydrogen or lower alkyl.
7. The compound according to 5, wherein $R_6$ is pyrrolidine.
8. A pharmaceutical composition, comprising as an active ingredient one or more of the compounds having the formula (I) as claimed in claim 1, and a pharmaceutically acceptable carrier.
9. A method of treating psychosis, depression, anxiety or drug abuse, which comprises the step of administering to a patient in need thereof an effective amount of the compound having the formula (I) as claimed in claim 1.

* * * * *